(12) United States Patent
Tanaka

(10) Patent No.: US 8,287,449 B2
(45) Date of Patent: Oct. 16, 2012

(54) ENDOSCOPE DEVICE

(75) Inventor: Yoshihisa Tanaka, Kofu (JP)

(73) Assignee: ARS Co., Ltd., Yamanashi (JP)

( * ) Notice: Subject to any disclaimer, the term of this patent is extended or adjusted under 35 U.S.C. 154(b) by 856 days.

(21) Appl. No.: 11/915,468

(22) PCT Filed: May 26, 2005

(86) PCT No.: PCT/JP2005/009633
§ 371 (c)(1),
(2), (4) Date: Apr. 13, 2009

(87) PCT Pub. No.: WO2006/126265
PCT Pub. Date: Nov. 30, 2006

(65) Prior Publication Data
US 2009/0209820 A1   Aug. 20, 2009
US 2010/0049000 A2   Feb. 25, 2010

(51) Int. Cl.
*A61B 1/01* (2006.01)
(52) U.S. Cl. ......... 600/149; 600/118; 600/131; 600/146
(58) Field of Classification Search .................. 600/118, 600/131, 145–152
See application file for complete search history.

(56) References Cited

U.S. PATENT DOCUMENTS

| | | | |
|---|---|---|---|
| 2,453,862 A * | 11/1948 | Salisbury | 600/146 |
| 3,605,725 A * | 9/1971 | Bentov | 600/434 |
| 4,721,099 A | 1/1988 | Chikama | |
| 5,846,183 A | 12/1998 | Chilcoat | |
| 6,283,757 B1 * | 9/2001 | Meghnot et al. | 434/33 |
| 2003/0027641 A1 * | 2/2003 | Parsons | 464/139 |
| 2004/0260292 A1 * | 12/2004 | Orbay et al. | 606/69 |
| 2007/0225562 A1 * | 9/2007 | Spivey et al. | 600/121 |
| 2007/0250110 A1 * | 10/2007 | Lu et al. | 606/205 |
| 2008/0045803 A1 * | 2/2008 | Williams et al. | 600/204 |
| 2011/0179915 A1 * | 7/2011 | Peng | 81/177.75 |

FOREIGN PATENT DOCUMENTS

| | | |
|---|---|---|
| JP | S51-035584 | 3/1976 |
| JP | 11-023981 A | 1/1999 |
| JP | 2002-125918 A | 5/2002 |

OTHER PUBLICATIONS

Supplementary search report issue by the European Patent Office in patent application EP 05743799.8, Aug. 26, 2010.
International Preliminary Report on Patentability issued in PCT/JP2005/009633, Mar. 14, 2008.

* cited by examiner

*Primary Examiner* — Matthew J Kasztejna
*Assistant Examiner* — Kevin G Barry, III
(74) *Attorney, Agent, or Firm* — Browdy and Neimark, PLLC

(57) ABSTRACT

An endoscope device having a control unit and a bendable probe unit arranged at the distal end of a wire extending from the control unit. The control unit includes a ball shaft and a control lever arranged on the ball shaft. The ball shaft includes a ball member and an outer case that encases the ball member and rotates along the outer peripheral surface of the ball member when the control lever is tilted. The wire is attached to the outer case. The construction facilitates control unit operation, which reduces inspection time and improves inspection accuracy.

11 Claims, 9 Drawing Sheets

(a)

(b)

ENDOSCOPE DEVICE

TECHNICAL FIELD

The present invention relates to an, endoscope device having a control unit and a bendable probe unit arranged at the distal end of a wire extending from the control unit.

BACKGROUND ART

Modern endoscope devices are used in a wide range of applications. In medical fields, they are used to provide diagnosis and treatment in the body. In industrial fields, they are used to inspect and repair machines and the interior of pipes. Endoscope devices are also used for rescue purposes during disasters; they are used in the search for victims trapped within collapsed buildings.

A typical endoscope device has a control unit and a probe unit arranged at the distal end of a wire that extends from the control unit (See Patent Document 1). The control unit includes a pair of operation knobs for bending the distal end of the probe unit vertically and horizontally. One operation knob can be rotated to pull one of the wires connected to that knob to bend the distal end of the probe unit vertically. Similarly, the other operation knob can be rotated to pull the other wire connected to that knob to bend the distal end of the probe unit horizontally. Thus, an operator can inspect a space in a vertical or horizontal direction by rotating the pair of operation knobs. To inspect the intermediate ranges between the vertical and horizontal directions, the operator will rotate the control unit itself to rotate the probe unit within the same plane. The wire is inserted within a flexible tube along with a camera cable for imaging. The distal end of the flexible tube, along with the wire, is connected to the probe unit while the proximal end of the flexible tube, along with the wire, is connected to the control unit. This construction enables the operator to cover almost 360° of the space by rotating the operation knobs of the control unit to bend, the probe unit and by rotating the control unit itself to rotate the probe unit, along with the flexible tube, within the same plane.

In conventional endoscope devices, however, the vertical and the horizontal bending movements of the distal probe unit are independently controlled by the individual operation knobs, so that when the operator attempts to, for example, redirect the vertically bent distal probe unit in the horizontal direction, the distal probe unit must first be brought back into the straight position before it is bent in the horizontal direction. This is a complex and time-consuming procedure.

In addition, when inspecting the intermediate ranges between the vertical and the horizontal directions of the probe unit in a conventional endoscope device, the operator must rotate both the control unit and the flexible tube to ensure that the probe unit rotates within the same plane. This forces the operator to hold the control unit and the flexible tube in both hands. Furthermore, the accuracy of inspection may vary significantly depending on the skill of the operator, making it difficult to maintain consistent inspection results.

Patent Document 1 Japanese Patent Application Laid-Open No. 2002-125918

DISCLOSURE OF THE INVENTION

Problems to be Solved by the Invention

Accordingly, it is an object of the present invention to provide an endoscope device that enables the operator to bend the distal probe unit in the vertical or horizontal direction, as well as in the intermediate ranges between the vertical and horizontal directions, by simply manipulating a single control lever with one hand. Not only does such an endoscope device eliminate the complex procedure required by conventional endoscope devices and decrease the time for inspection, but it also improves the inspection accuracy and enables the maintenance of consistent inspection results.

Means for Solving the Problems

To achieve the above-described object, the endoscope device in accordance with the present invention has a control unit and a bendable probe unit arranged at the distal end of a wire extending from the control unit. The control unit includes a ball shaft and a control lever arranged on the ball shaft. The ball shaft includes a ball member and an outer case that encases the ball member and rotates along the outer peripheral surface of the ball member by the tilting action of the control lever. The wire is attached to the outer case.

The endoscope device of the present invention also includes a stopper mechanism between the ball shaft and the control lever for restricting rotation of the outer case.

The endoscope device of the present invention also includes on the ball shaft an anti-twist mechanism for preventing the wire from becoming twisted when the outer case is rotated horizontally.

Effect of the Invention

In the endoscope device in accordance with the present invention, the direction and angle of bending of the probe unit can be freely controlled by manipulating the wires by means of the ball shaft and the control lever. That is to say, by tilting the single control lever arranged on the ball shaft in the vertical or horizontal direction or anywhere in between the two directions, the probe unit is bent correspondingly to the direction and angle of tilting of the control lever. The endoscope device in accordance with the present invention can also rotate the probe unit horizontally with the probe unit bent, in one direction. Thus, the endoscope device of the present invention achieves high operability of the control unit. Use of the endoscope device of the present invention therefore reduces the burden of the operator, as well as the inspection time, while at the same time improving the accuracy of inspection.

BEST MODE FOR CARRYING OUT THE INVENTION

Figure 1:
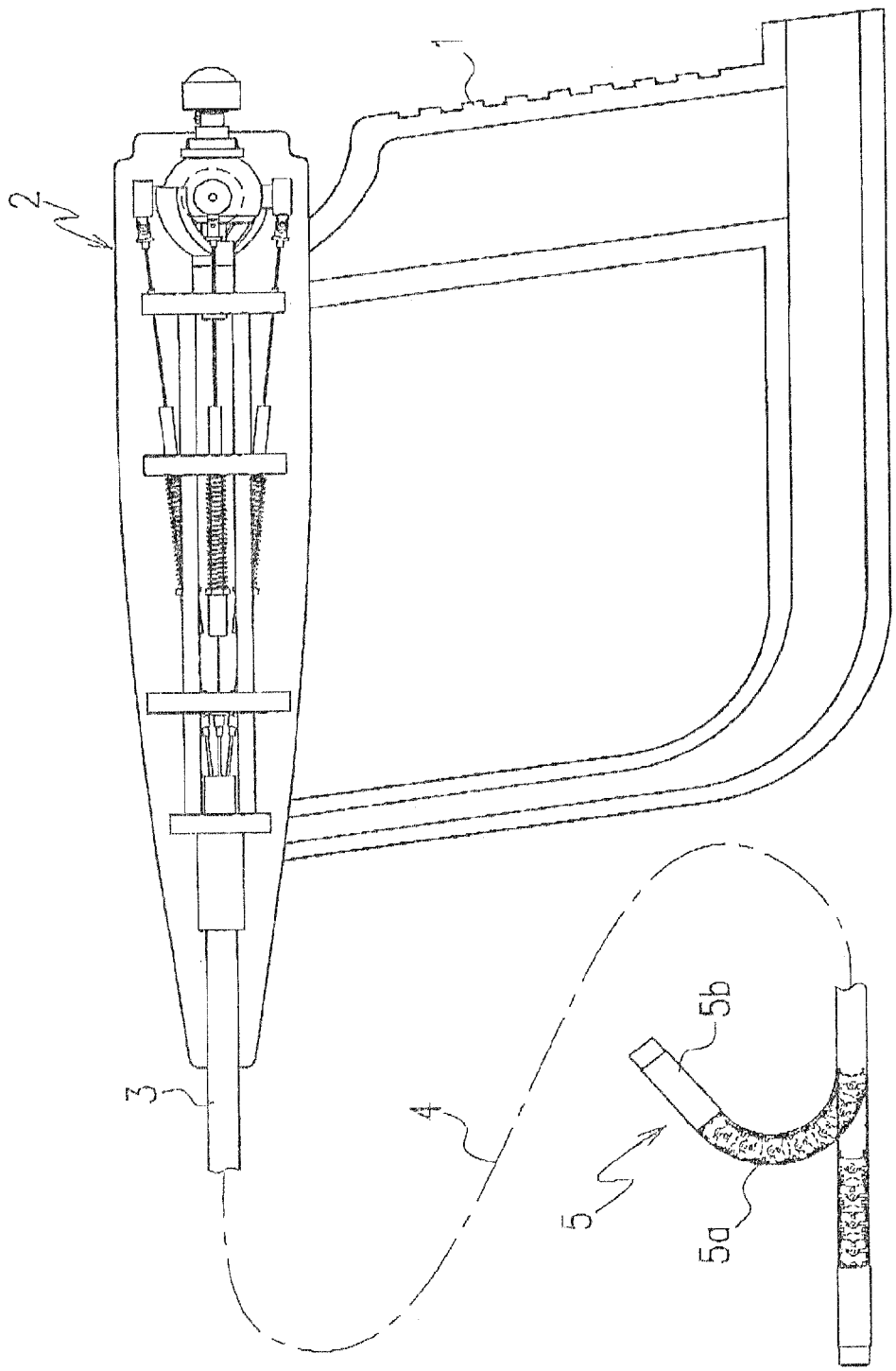
FIG. 1 is a schematic diagram showing the overall structure of an endoscope device in accordance with the present invention.

Embodiments of the endoscope device in accordance with the present invention will now be described in detail with reference to the accompanying drawings. Referring to FIG. 1, an endoscope device in accordance with the present invention includes a handle 1 and a pistol-shaped control unit 2 attached to the handle 1. The control unit 2 is connected to a distal probe unit 5 by means of a wire 4 passed through a flexible tube 3. FIGS. 2 through 5 show detailed structures of the control unit 2. The control unit 2 includes a ball shaft 7 supported by a frame 6 and a control lever 8 arranged on the ball shaft 7. The frame 6 is composed of four vertically arranged plates 9a through 9d that are connected by a plurality of support bars 10. The uppermost first plate 9a includes an integrally formed cylindrical portion 11 that projects upward from the center of the first plate 9a.

Figure 4:
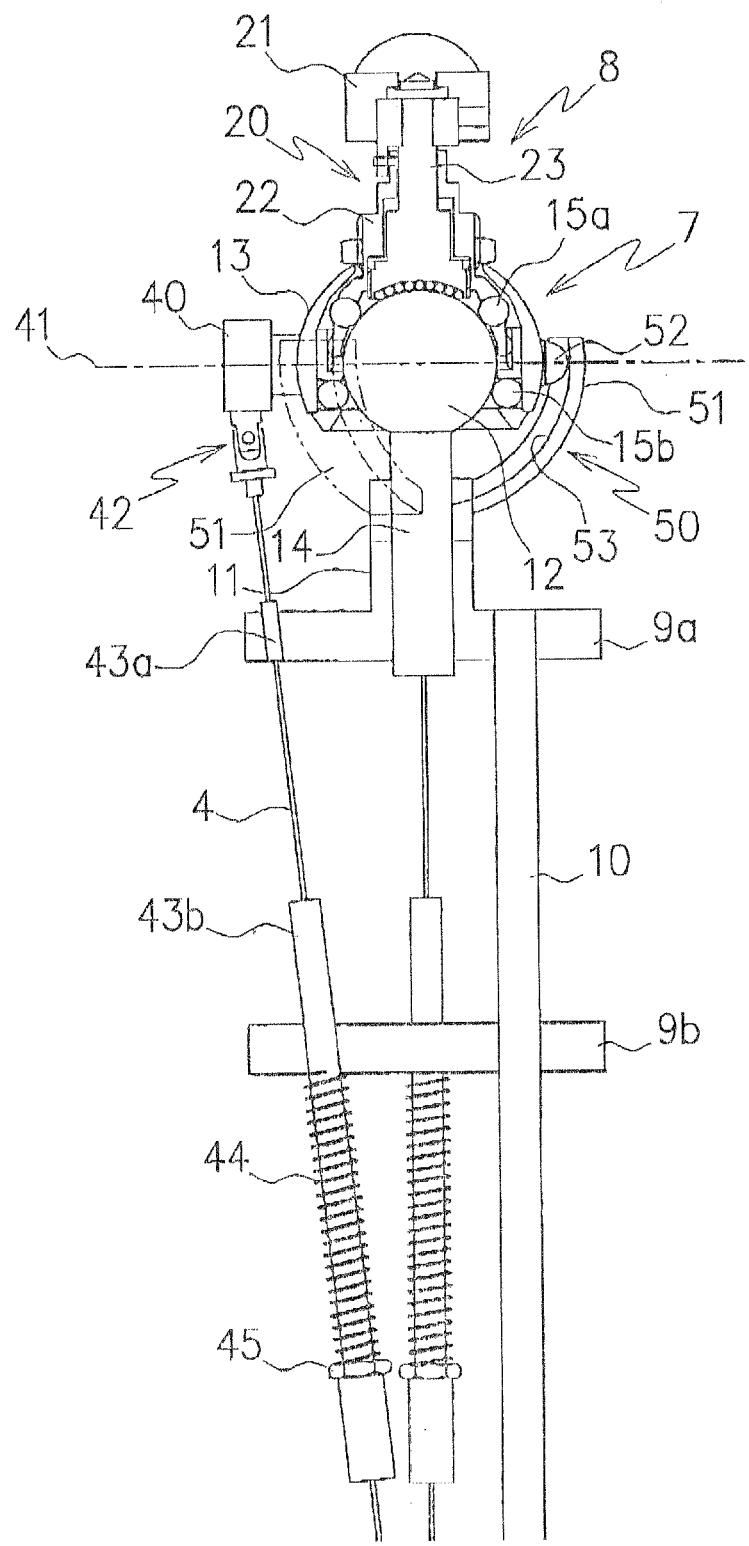
FIG. 4 is a cross-sectional view taken along line IV-IV of FIG. 3.
Figure 5:
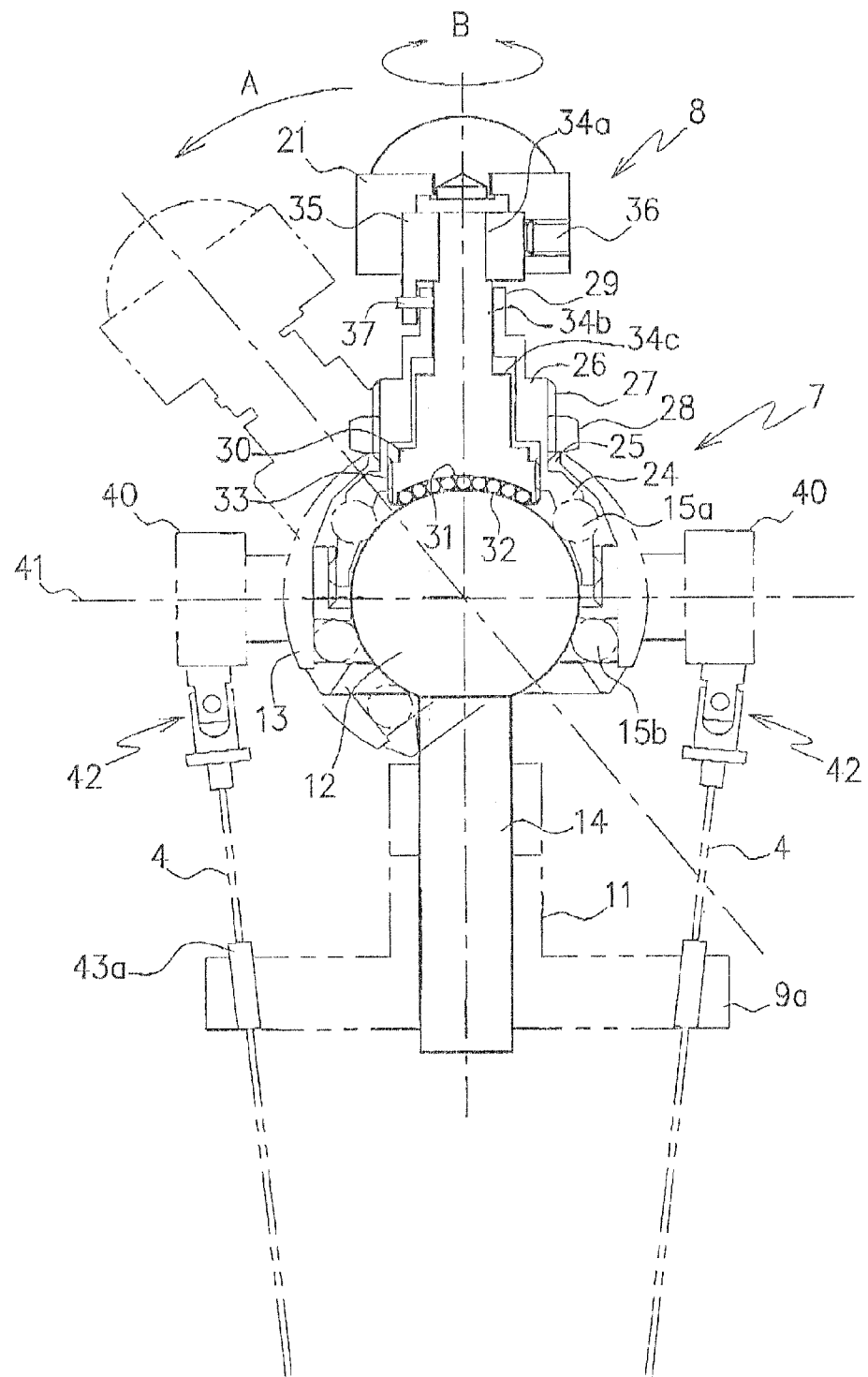
FIG. 5 is an enlarged view of major components of the endoscope device.

As shown in FIGS. 4 and 5, the ball shaft 7 includes a ball member 12 and an outer case 13 that encases the ball member 12 and, freely rotates along the outer peripheral surface of the ball member 12 by the tilting action of the control lever 8. In one example, the ball member 12 includes a stainless-steel ball joined to a rod-shaped neck portion 14 at the bottom thereof. The ball member 12 is secured to the frame 6 by inserting the neck, portion 14 into the cylindrical portion 11 of the first plate 9a.

The outer case 13 of the ball shaft 7 is a substantially dome-shaped hemisphere with an open bottom. The outer case 13 is mounted so that a gap is formed between the outer case 13 and the outer peripheral surface of the ball member 12. Rolling elements 15a, 15b such as steel balls are arranged in the gap on the upper part and the lower part of the ball member 12 to form a ball bearing that enables the outer case 13 to smoothly rotate along the outer peripheral surface of the ball member 12. In one example, the outer case 13 is formed of the same stainless steel used to form the ball member 12.

The control lever 8 is arranged at the upper end of the outer case 13. The control lever 8 is provided above the ball shaft 7 and includes a control shaft 20 secured to the upper end of the outer case 13 and a knob member 21 attached to the upper end of the control shaft 20. In this embodiment, the control lever 8 controls the rotation of the outer case 13 and forms a part of the stopper mechanism that restricts rotation of the outer case 13. The specific construction of the control lever 8 is as follows: The control shaft 20 of the control lever 8 has a double structure consisting of an outer sheath member 22 directly secured to the upper end of the outer case 13 and a stopper shaft 23 inserted, in the outer sheath member 22. The outer sheath member 22 has at its lower end a skirt portion 24 that flares downward and extends through a mounting hole 25 formed at the upper end of the outer case 13 into the gap between the ball member 12 and the outer case 13. The skirt portion 24 holds the rolling elements 15a on the upper part. The rolling elements 15a are in contact with the outer peripheral surface of the ball member 12. A lower outer sheath member 26 formed at the upper end of the skirt portion 24 extends upward through the mounting hole 25 of the outer case 13. The lower outer sheath member 26 includes an external thread 27 formed on its outer peripheral surface to which a nut 28 is fastened to position the skirt portion 24 and secure the outer sheath member 22 to the outer case 13.

The stopper shaft 23 has a profile that substantially corresponds to the interior of the outer sheath member 22. The stopper shaft 23 has at its lower end a base portion 30 with a large area. The bottom surface of the base portion 30 is formed as a curved recess 31 that corresponds to the curve of the ball member 12 and houses a number of rolling elements 32 that serve as a press-enhancing member. In one example, the rolling elements 32 are steel balls that are smaller in size than the rolling elements 15a, 15b arranged between the ball member 12 and the outer case 13. The rolling elements 32 are held in contact with the upper outer peripheral surface of the ball member 12. A screw engagement portion 33 is provided between the outer surface of the base portion 30 and the corresponding inner surface of the skirt portion 24 to allow the stopper shaft 23 to be vertically moved. The stopper shaft 23 includes three stepped shaft portions 34a, 34b, and 34c above the base portion 30. The lower shaft portion 34c is arranged with a small gap formed between the lower outer sheath member 26 and the lower shaft portion 34c. The middle shaft portion 34b is slidably received within an upper outer sheath member 29. The upper shaft portion 34a extends past the upper outer sheath member 29 and has the knob member 21 attached, thereto by a collar 35. The knob member 21 is secured to the collar 35 by means of a stopper screw 36. A stopper pin 37 is arranged between the collar 35 and the shaft portion 34b of the stopper shaft 23 to restrict the rotation of the stopper shaft 23 to a certain degree. In addition to the rolling elements 32, a rubber sheet may be used as the press-enhancing member.

The control lever 8 having the above-described construction shown in FIG. 5 can be tilted in the direction A indicated by an imaginary line as an integral unit of the outer sheath member 22 and the stopper shaft 23. Since the outer sheath member 22 is secured to the outer case 13, the outer case 13 can be rotated on the outer peripheral surface of the ball member 12 by tilting the control lever 8. In other words, the outer case 13 can be rotated along the outer peripheral surface of the ball member 12 in a desired direction and to a desired degree by tilting the control lever 8 in the desired direction and to the desired degree.

In this embodiment, the construction of the control lever 8 shown in FIG. 5 allows the knob member 21 to be turned in the direction B to thereby turn the stopper shaft 23 and at the same time move the stopper shaft 23 vertically with respect to the outer sheath member 22 by the action of the screw engagement portion 33 between the base portion 30 and the skirt portion 24. In other words, by turning the knob member 21 in one direction, the stopper shaft 23 can be moved downward so that the plurality of rolling elements 32 housed in the recess 31 at the bottom surface of the base portion 30 are pressed against the upper outer peripheral surface of the ball member 12 to restrict tilting of the control lever 8. By turning the knob member 21 in the other direction, the stopper shaft 23 can be moved upward so that the rolling elements 32 remain in contact with the outer peripheral surface of the ball element 12 but allow the outer case 13 to rotate smoothly. By pressing the rolling elements 32 against the ball member 12 with an appropriate pressure, the control lever 8 can be tilted in a semi-braked state. The screw engagement portion 33 also serves as a means for maintaining the control lever 8 in a pressed state.

Figure 2:
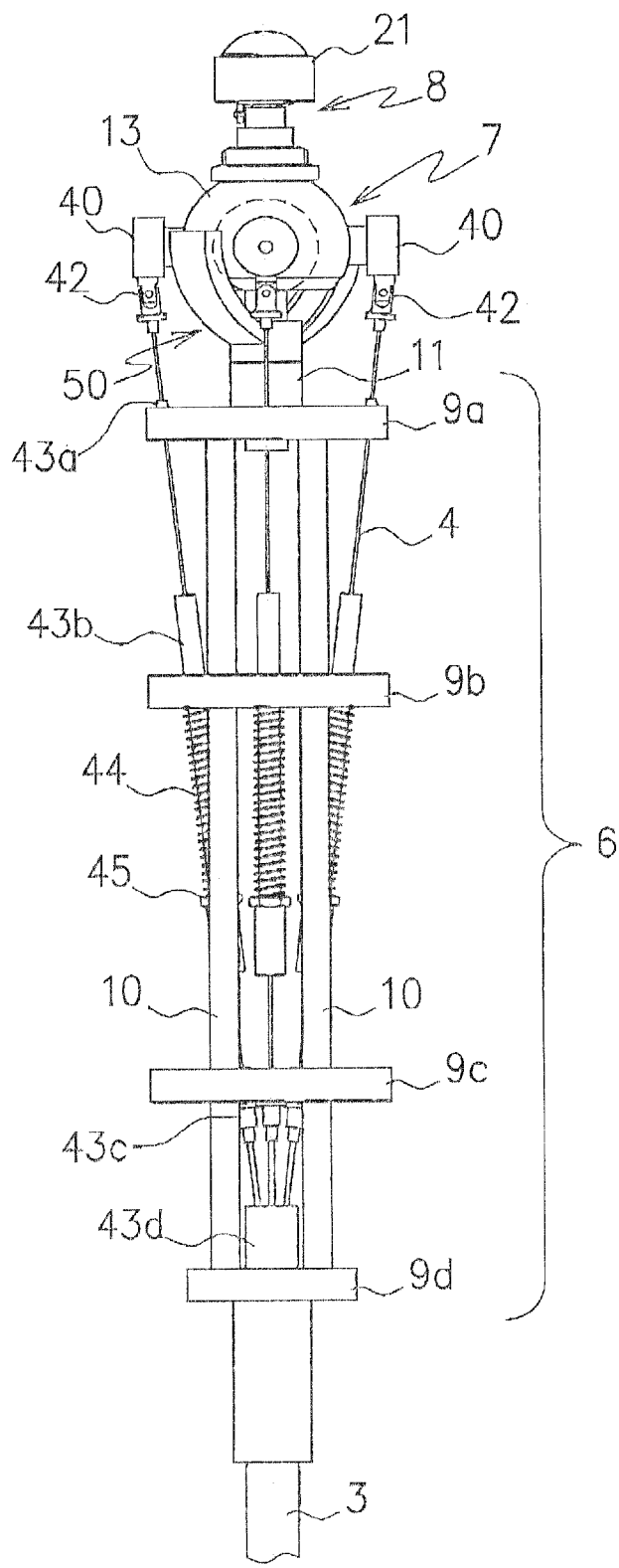
FIG. 2 is a front view showing the overall construction of the control unit of the endoscope device.

Connectors 40 to which the proximal ends of the respective wires 4 are attached are attached to the outer peripheral surface of the outer case 13. The connectors 40 are arranged along approximately the center line 41 of the outer peripheral surface of the outer case 13 at four equally spaced positions. The proximal end of each wire 4 is pivotably attached to one of the connectors 40 by a universal joint 42. Each wire 4 is inserted within the flexible tube 3 along with a camera cable for imaging (not shown) and is connected to the probe unit 5 arranged at the distal end of the flexible tube 3. Within the control unit 2, the wires 4 are supported by the four plates 9a through 9d that together form the frame 6. As shown in FIG. 2, through tubes 43a through 43d are arranged through the respective plates 9a through 9d for supporting the wires 4 placed therethrough. The wires 4 are each secured to one of the through tubes 43b arranged through the second plate 9b, so that the through tubes 43b move vertically relative to the second plate 9b as the wires 4 are pulled and moved vertically. A coil spring 44 is wound about the part of each of the through tubes 43b below the second plate 9b. The bottom surface of the second plate 9b and nuts 45 arranged at the lower end of the coil springs 44 serve as upper and lower stoppers for the coil springs 44, respectively. Accordingly, when the wires 4 and thus, the through tubes 43b, are pulled, the coil springs 44 contract, to cause tension. Conversely, when the wires 4 are released, the coil springs 44 recover to move the through tubes 43b and the wires 4 downward back into their original positions.

The wires 4 are arranged within the control unit 2 in a tapered manner in which they come increasingly close to one another as they extend from the first plate 9a to the fourth plate 9d where they are brought together in the single through tube 43d that is provided through the fourth plate 9d. This tapered arrangement of the wires 4 helps reduce friction during pulling of the wires 4 and ensures the smooth movement of the wires 4. Although four wires 4 are used in this embodiment, three wires may be used to provide similar pulling functions.

Figure 3:
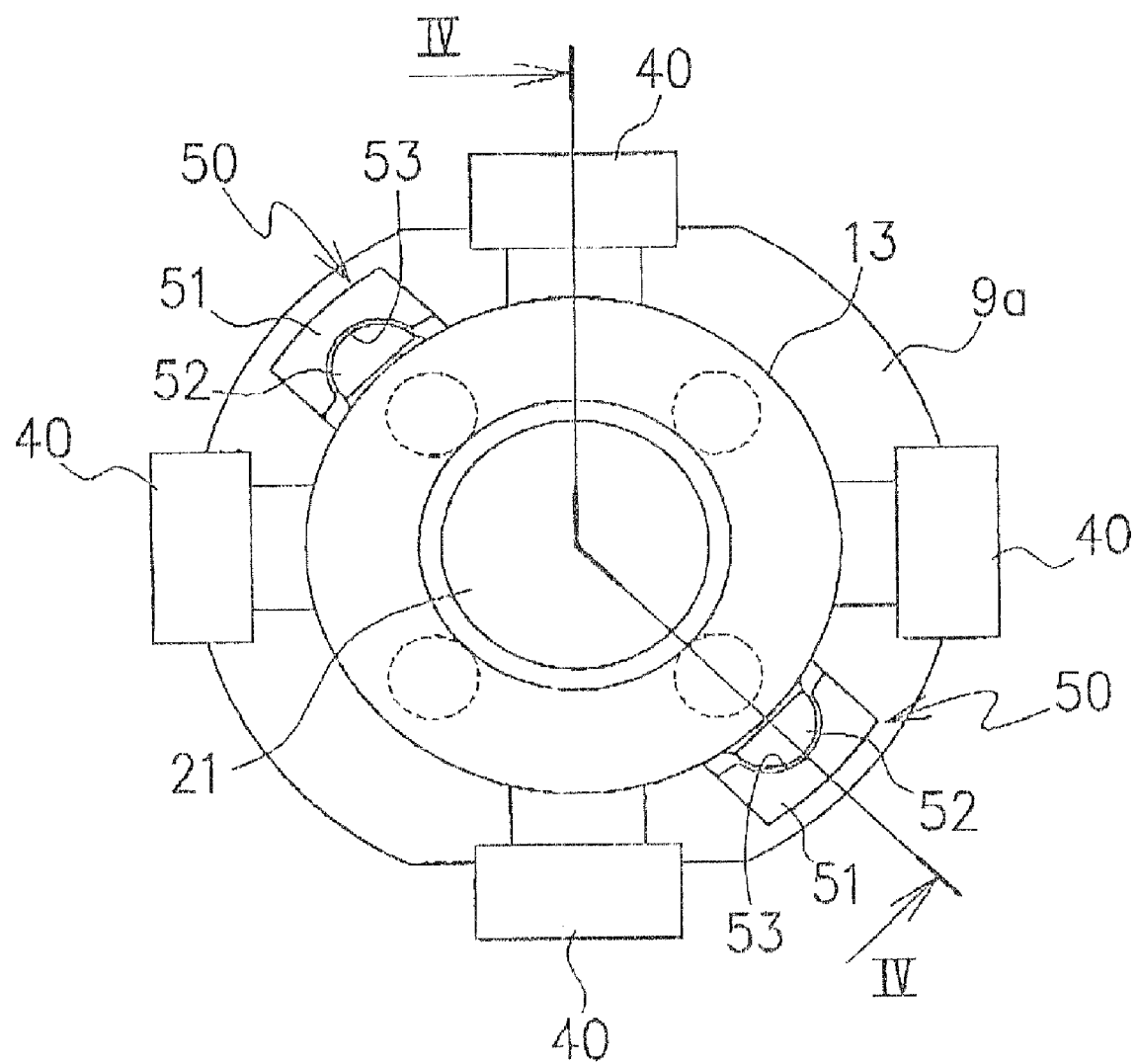
FIG. 3 is a plan view of the control unit of the endoscope device.

In this embodiment, the ball shaft 7 also includes an anti-twist mechanism 50 for preventing the wires 4 from becoming twisted when the outer case 13 is rotated. As shown in FIGS. 2 through 4, the anti-twist mechanism 50 is composed of a guide member 51 that extends from the neck portion 14 of the ball member 12 along the outer peripheral surface of the outer case 13 and a hemispherical projection portion 52 formed on the outer peripheral surface of the outer case 13. The guide member 51 is composed of a plate-shaped member that has a predetermined width and has a curved shape corresponding to the curve of the outer peripheral surface of the outer case 13. The guide member 51 has its one end secured to the neck portion 14 of the ball member 12 with the other end extending to approximately the center line 41 of the outer case 13. As shown in FIG. 4, a pair of guide members 51 are arranged, one across the outer case 13 from the other, at positions horizontally offset by 45 degrees from the respective wire connectors 40. Each guide member 51 includes on its Inner peripheral surface a continuous guide groove 53 that extends along the length of the guide member 51. The guide groove 53 consists of a groove that is formed in the guide member 51 and has an approximately semicircular cross-section.

As shown in FIGS. 3 and 4, a pair of projection portions 52 are arranged at positions corresponding to the pair of guide members 51. The pair of projection portions 52 slidably engage with the respective guide grooves 53 formed on the pair of guide members 51. As shown in FIG. 4, the projection portions 52 are each arranged on approximately the center line 41 of the outer case 13 so that they are positioned near the upper ends of the respective guide grooves 53 when the control lever 8 is in the upright position. The projection portions 52 are not limited to the hemispherical projection portions secured to the outer peripheral surface of the outer case 13. For example, they may be spheres rotatably embedded in the outer case 13 with a portion projecting from the 1 outer case 13.

Figure 6:
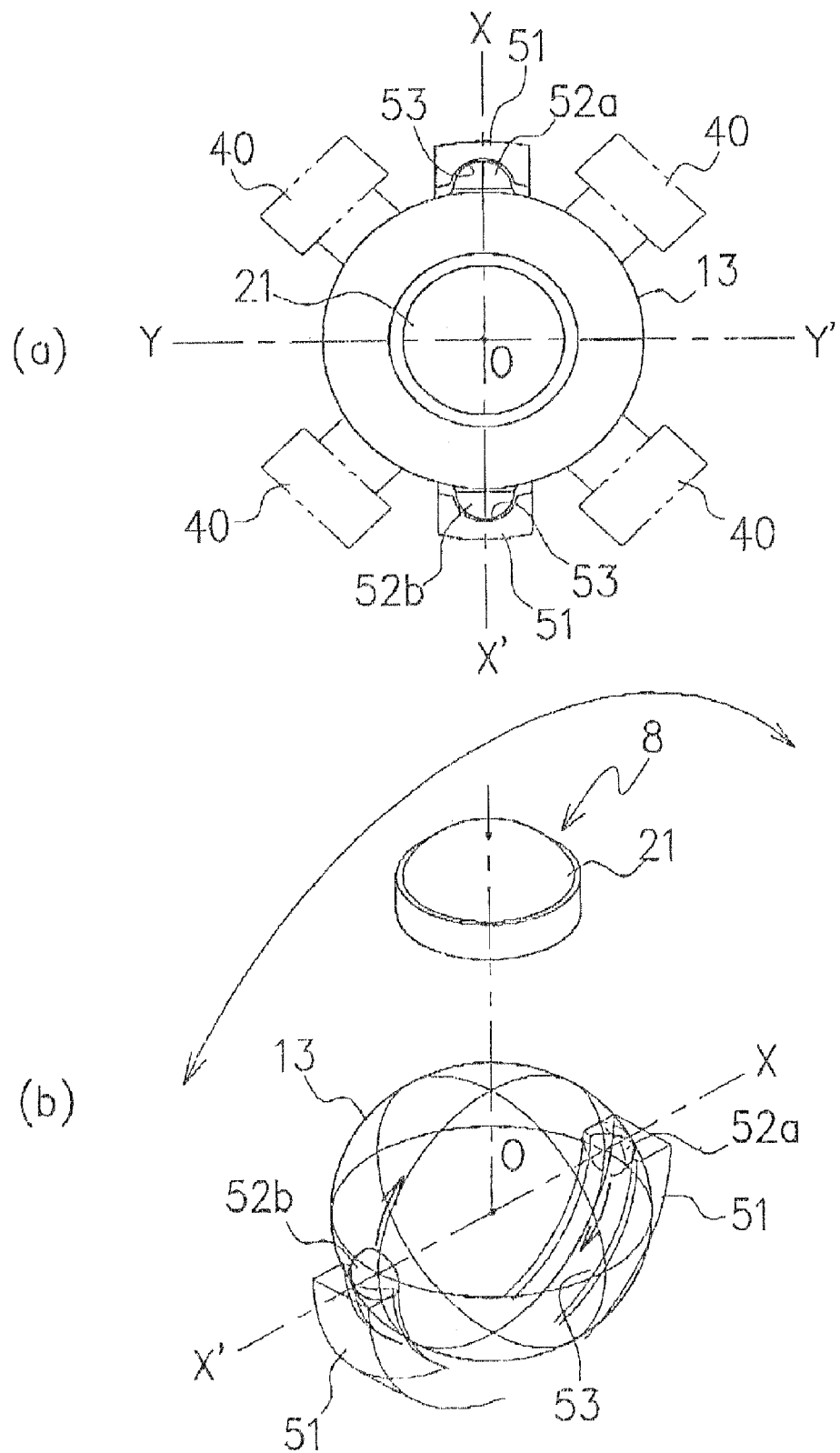
FIG. 6 is an illustrative diagram showing the action of the anti-twist mechanism when the control lever is tilted in the direction of the X-X' axis.
Figure 7:
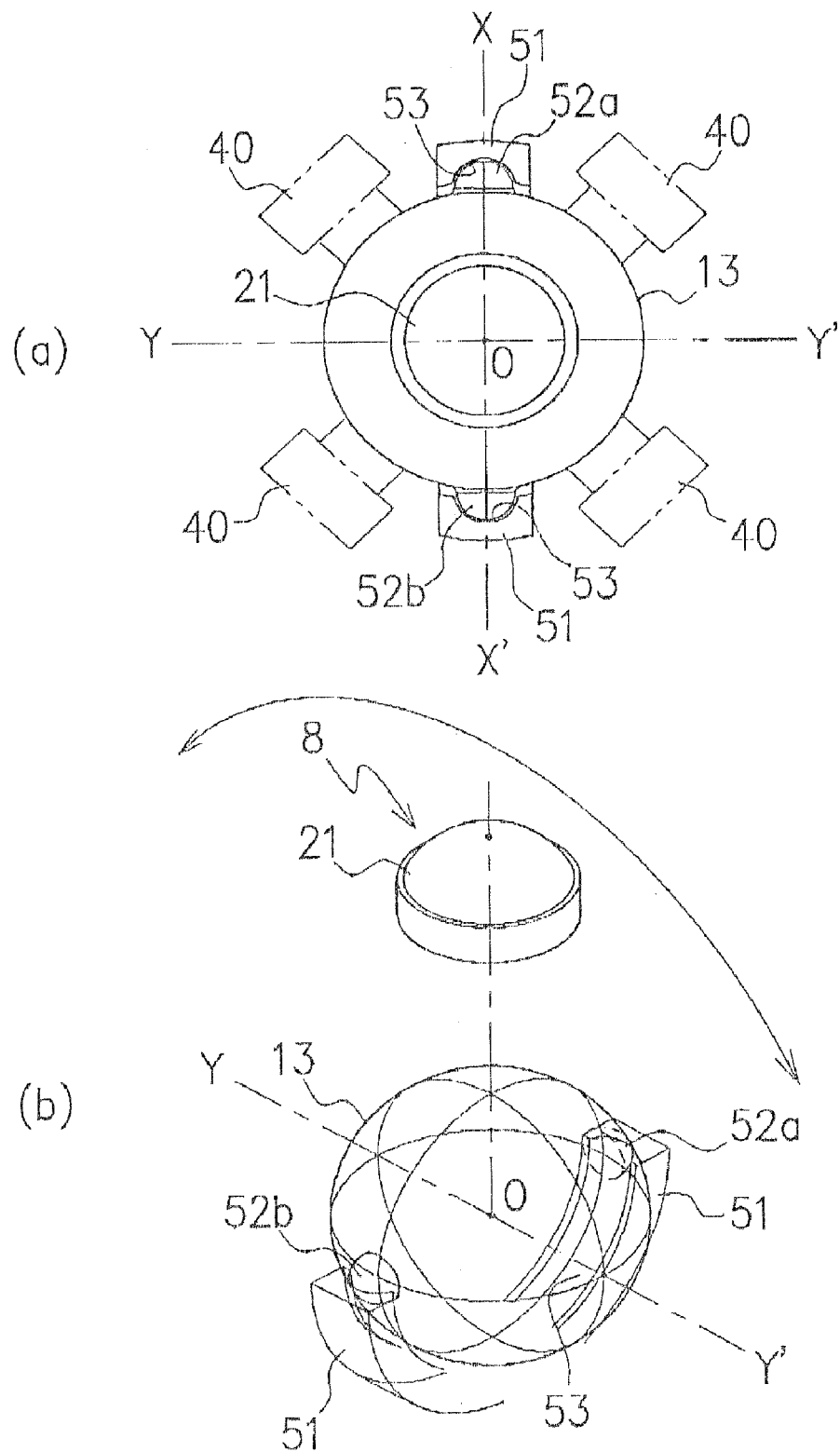
FIG. 7 is an illustrative diagram showing the action of the anti-twist mechanism when the control lever is tilted in the direction of the Y-Y' axis.
Figure 8:
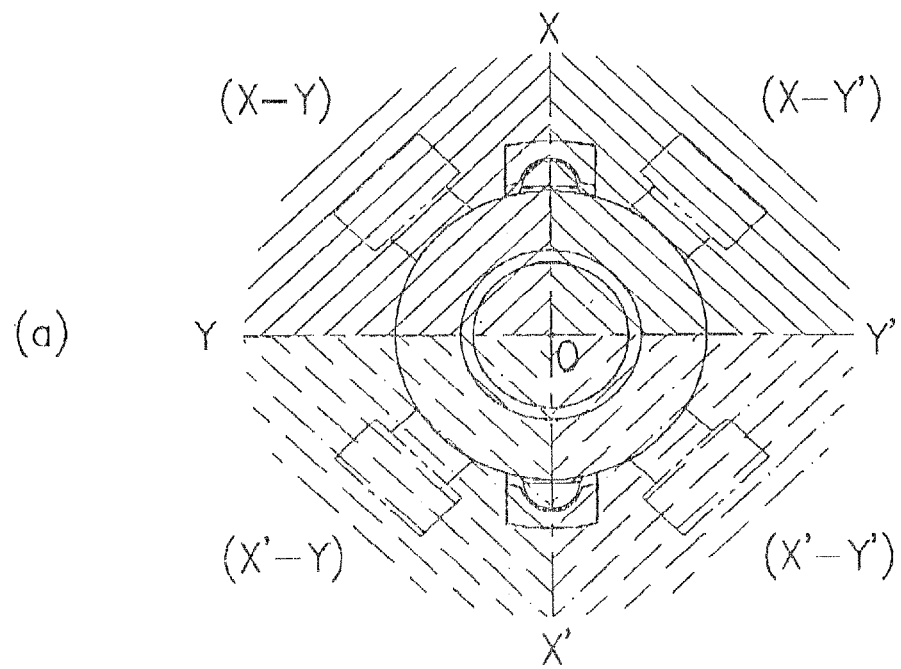
FIG. 8 is an illustrative diagram showing the action of the anti-twist mechanism when the control lever is tilted in the intermediate range between the X-X' axis direction and the Y-Y' axis direction.
Figure 8:
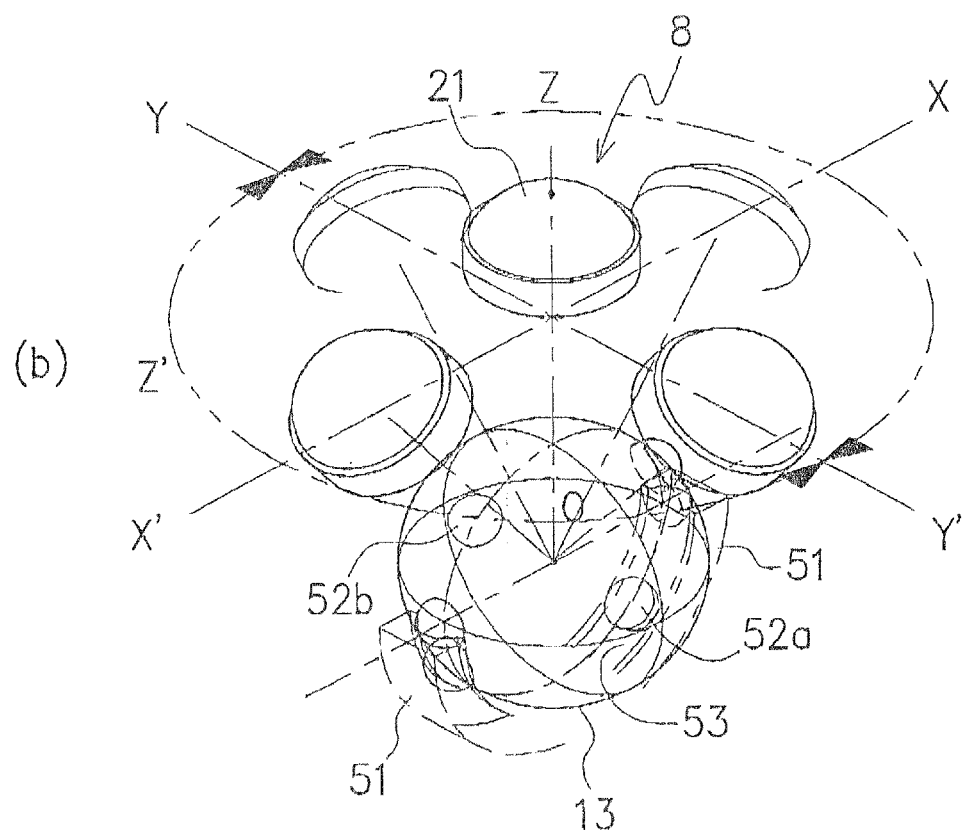

FIGS. 6 through 8 illustrate how the anti-twist mechanism 50 configured as described above works. FIGS. 6(a) and (b) depict a case where the outer case 13 is rotated in the direction of the X-X' axis along which the anti-twist mechanism 50 is arranged. When the knob member 21 of the control lever 8 is tilted, for example, in the direction X, one of the projection portions 52b positioned away from the direction X comes out of the guide groove 53, The other projection portion 52a, however, slides downward in the guide groove 53, allowing the outer case 13 to rotate in the direction X.

FIGS. 7(a) and (b) depict a case where the outer case 13 is rotated in the Y-Y' axis direction orthogonal to the X-X' axis direction. In this case, both of the right and left projection portions 52a and 52b remain engaged with the guide grooves 53 whether the control lever 3 is tilted in the direction Y or in the direction Y'. In this manner, the projection portions 52a and 52b can serve as pivots, allowing the outer case 13 to rotate in the Y-Y' axis direction.

FIGS. 8(a) and (b) depict a case where the outer case 13 is rotated in the intermediate range between the X-X' axis direction and the Y-Y' axis direction. As in the above-described case where the control lever 8 is tilted in the direction X, tilting the control lever 8 in a predetermined direction causes one of the projection portions (in this case, the projection portion 52b) to come out of the guide groove 53 and the other projection portion (in this case, the projection portion 52a) to slide in the guide groove 53, The overall tilting action of the control lever 8, when closely examined in quadrants, is as follows: When the control lever 8 is tilted in the X-Y quadrant or in the X-Y' quadrant, the projection portion 52b comes out of the guide' groove 53 while the projection portion 52a slides in the guide groove 53 to allow the outer case 13 to rotate. Conversely, when the control lever 8 is tilted in the X'-Y quadrant or in the X'-Y' quadrant, the projection portion 52a comes out of the guide groove 53 while the projection portion 52b slides in the guide groove 53 to allow the outer case 13 to rotate. In this manner, the control lever 8 can be tilted in any desired direction to correspondingly rotate the outer case 13.

As shown in FIG. 8, the anti-twist mechanism 50 allows the control lever 8 to be rotated in the horizontal direction when the control lever 8 is tilted. That is to say, when one of the projection portions (52b) is disengaged from the guide groove 53 with the other projection portion (52a) being guided by the guide groove 53, the control lever 8 can be rotated in the direction Z within the X-Y quadrant and the X-Y' quadrant, causing the outer case 13 to rotate correspondingly. Conversely, when the projection portion 52a is disengaged from the guide groove 53 and the projection portion 52b is being guided by the guide groove 53, the control lever 8 can be rotated in the direction Z' within the X'-Y quadrant and. the X'-Y' quadrant to cause the outer case 13 to rotate correspondingly. In this manner, the control lever 8 can be rotated in a desired direction to correspondingly rotate the outer case 13 in a horizontal direction.

As described above, the anti-twist mechanism 50 allows the control lever 8 to be rotated in the direction Z or in the direction Z' by switching the projection portion (52a or 52b) guided by the guide groove 53 from one to the other as the control lever 8 is rotated in the horizontal direction. At the same time, the anti-twist mechanism 50 serves to prevent a free 360-degree rotation of the control lever 8, thus preventing twisting of the wires 4.

Figure 9:
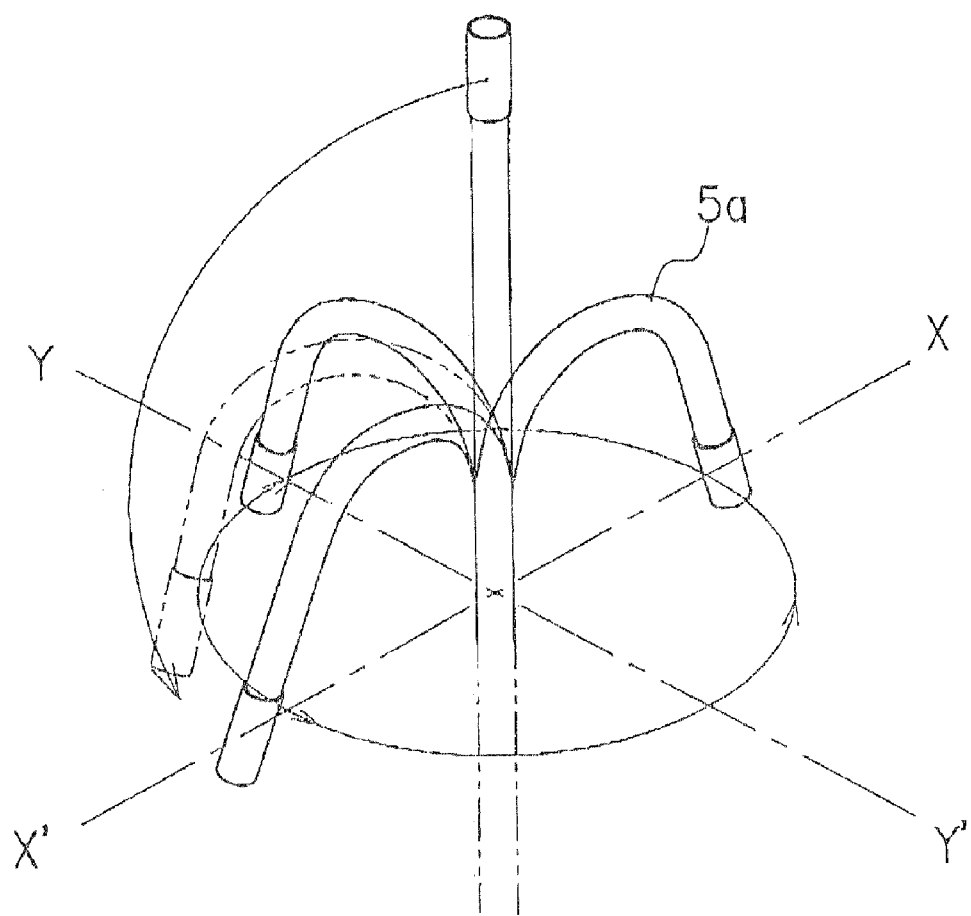
FIG. 9 is a perspective view showing the angle portion bending correspondingly to the manipulation of the control unit.

The operation of the control unit 2 configured as described above will now be described. As shown in FIG. 1, the probe unit 5 connected to the distal end of the wires 4 includes an angle portion 5a that can bend in any direction and a camera unit 5b arranged at the distal end of the angle portion 5a. The control unit 2 is connected to the angle portion 5a by the four wires 4 inserted within the flexible tube 3. The angle portion 5a can be bent in a desired direction and to a desired degree by tilting the control lever 8 of the control unit 2. For example, tilting the control lever 8 in the direction of the X-X' axis or Y-Y' axis causes the outer case 13 to rotate in that direction. As a result, one of the wires 4 positioned away from the direction of tilting is pulled strongly. As the corresponding wire 4 is pulled in the angle portion 5a, the angle portion 5a bends in the direction of the X-X' axis or Y-Y' axis, as shown in FIG. 9. The operator may align the direction of tilting of the control lever 8 with the direction of bending of the angle portion 5a to facilitate operation.

The control lever 8 may also be tilted in the intermediate region, between the X-X' axis and the Y-Y' axis. As in the above-described case, the pulled wires 4 cause the angle portion 5a to bend in the corresponding direction (the direction indicated by an imaginary line in FIG. 9). In this manner, the angle portion 5a can. be freely bent in any desired direction by tilting the control lever 8 in that direction. The endoscope device of the present invention therefore achieves high maneuverability since the direction and angle of tilting of the control lever 8 correspond to the direction and angle of bending of the angle portion 5a. In addition, the endoscope device of the present invention allows the angle portion 5a to be rotated in its bent position as shown in FIG. 9 by horizontally rotating the control lever 8 in its tilted position. This construction eliminates the need to rotate the control unit and the flexible tube as required in conventional endoscope devices.

The action of the stopper mechanism of the control unit 2 will now be described. The stopper mechanism is advantageous when it is desired, for example, to keep the angle portion 5a bent. In such a case, the operator, with his thumb and index finger, turns the knob member 21 of the control lever 8 in one direction so as to rotate and move the stopper shaft 23 of the control lever 8 downward. This causes the rolling elements 32 arranged in the recess 31 at the bottom surface of the stopper shaft 23 to be pressed against the upper outer peripheral surface of the ball member 12. If the operator attempts to rotate the outer case 13 in this state, the friction between the upper outer peripheral surface of the ball member 12 and the rolling elements 32 restricts movement of the outer case 13, making it impossible for the operator to manipulate the control lever 8. As a result, the angle portion 5a remains bent. In some cases, the operator may wish to rotate the outer case 13 in a semi-braked state without completely restricting movement of the outer case 13, This occurs when the operator wishes to continuously capture lateral images by swinging the angle portion 5a sideways while keeping the angle portion 5a bent at a certain angle, in such a case, the operator turns the knob member 21 to a degree that the rolling elements 32 are lightly pressed against the upper outer peripheral surface of the ball member 12, with the position of the control lever 8 being maintained by the screw engagement portion 33. In this manner, the control lever 8 is kept in a semi-braked state.

Industrial Applicability

The endoscope device of the present invention using a ball shaft in its control unit allows the operator to freely bend the wire-operated angle portion in any desired direction, as well as to rotate the angle portion while it is bent. The endoscope device of the present invention thus offers a highly maneuverable control unit that not only reduces the burden of the operator, but also decreases the time required for inspection and improves inspection accuracy. The present invention should therefore find wide applications not only in medical fields, but also in various industrial fields and emergency applications during disasters.

REFERENCE NUMERALS

2 Control unit
4 Wire
5 Probe unit
5a Angle portion
7 Ball shaft
8 Control lever
12 Ball member
15a, 15b Rolling element
20 Control shaft
22 Outer sheath member
23 Stopper shaft
32 Rolling element
33 Screw engagement portion
50 Anti-twist mechanism
51 Guide member
52a, 52b Projection portion
53 Guide groove

The invention claimed is:

1. An endoscope device, comprising:
a control unit, the control unit including a ball shaft and a control lever arranged on the ball shaft, and the ball shaft including a ball member and an outer case that encases the ball member and rotates along an outer peripheral surface of the ball member by a tilting action of the control lever;
a bendable probe unit arranged at a distal end of a wire extending from the control unit, the wire being attached to the outer case; and
an anti-twist mechanism provided between the outer case and the ball shaft and configured to prevent the wire from becoming twisted when the outer case is rotated,
wherein the anti-twist mechanism includes a pair of guide members provided on the ball shaft and extending only in one direction along an outer peripheral surface of the outer case and a pair of projection portions provided to be projected from the outer peripheral surface of the outer case and guided by guide grooves provided in the pair of guide members, at least one projection portion being configured to be capable of being disengaged with the corresponding guide groove of the guide member, when the outer case is rotated,
wherein at least one of the pair of projection portions is guided by the corresponding guide groove to limit the rotation of the outer case, when the outer case is rotated along the outer peripheral surface of the ball member.

2. The endoscope device according to claim 1, wherein at least three wires are secured to the outer case, each wire being pulled according to a direction and an angle of tilting of the control lever so as to control a direction and an angle of bending of the probe unit arranged at the distal end of the wires.

3. The endoscope device according to claim 1, wherein the outer case is mounted on the ball member with rolling elements arranged between the outer case and the ball member.

4. The endoscope device according to claim 1, including a stopper mechanism between the ball shaft and the control lever for restricting rotation of the outer case.

5. The endoscope device according to claim 4, wherein the control lever is pressed against the ball member of the ball shaft to operate the stopper mechanism.

6. The endoscope device according to claim 4, wherein in the stopper mechanism, the control lever is pressed against the ball member by turning the control lever.

7. The endoscope device according to claim 4, wherein the stopper mechanism includes a press-enhancing member that is arranged between the control lever and the ball member and enhances the pressing of the control lever against the ball member during operation of the stopper mechanism.

8. The endoscope device according to claim 7, wherein the press-enhancing member comprises a rolling element or a rubber sheet.

9. The endoscope device according to claim 4, wherein the stopper mechanism includes means for maintaining a position of the control lever when the control lever is pressed against the ball member of the ball shaft.

10. The endoscope device according to claim 9, wherein the maintaining means comprises a screw engagement portion that causes the control lever to move vertically relative to the ball member when the control lever is turned.

11. The endoscope device according to claim 1, wherein the wire is attached at a proximal end thereof to an outer peripheral surface of the outer case with a universal joint interposed therebetween.

* * * * *